US009892883B2

(12) United States Patent
Anno et al.

(10) Patent No.: US 9,892,883 B2
(45) Date of Patent: *Feb. 13, 2018

(54) ROTATING-ANODE X-RAY TUBE ASSEMBLY WITH COOLING SYSTEM

(71) Applicant: Toshiba Electron Tubes & Devices Co., Ltd., Otawara-shi (JP)

(72) Inventors: Hidero Anno, Otawara (JP); Masaji Kanagami, Utsunomiya (JP)

(73) Assignee: Toshiba Electron Tubes & Devices Co., Ltd., Otawara-shi (JP)

( * ) Notice: Subject to any disclaimer, the term of this patent is extended or adjusted under 35 U.S.C. 154(b) by 207 days.

This patent is subject to a terminal disclaimer.

(21) Appl. No.: 14/528,408

(22) Filed: Oct. 30, 2014

(65) Prior Publication Data

US 2015/0124936 A1     May 7, 2015

(30) Foreign Application Priority Data

Nov. 5, 2013    (JP) ................................. 2013-229327

(51) Int. Cl.
*H01J 35/16* (2006.01)
*H01J 37/16* (2006.01)
(Continued)

(52) U.S. Cl.
CPC ............ *H01J 35/105* (2013.01); *A61B 6/107* (2013.01); *A61B 6/4488* (2013.01); *H01J 7/26* (2013.01);
(Continued)

(58) Field of Classification Search
CPC .. A61B 6/00; A61B 6/107; A61B 6/40; A61B 6/44; A61B 6/4488; H05G 1/00;
(Continued)

(56) References Cited

U.S. PATENT DOCUMENTS

| 4,355,410 A | 10/1982 | Sullins |
| 6,361,208 B1 | 3/2002 | Takenaka et al. |
| 2009/0184267 A1* | 7/2009 | Bar ........................... F26B 3/28 250/504 R |

FOREIGN PATENT DOCUMENTS

| CN | 101494149 A | 7/2009 |
| GB | 755612 A | 8/1956 |

(Continued)

OTHER PUBLICATIONS

Extended European Search Report dated Mar. 31, 2015 in Patent Application No. 1490208.0.
(Continued)

*Primary Examiner* — Anastasia Midkiff
(74) *Attorney, Agent, or Firm* — Oblon, McClelland, Maier & Neustadt, L.L.P.

(57) ABSTRACT

According to one embodiment, a rotating-anode X-ray tube assembly includes a rotating-anode X-ray tube, a housing, a coolant, a first shell, an X-ray shielding member, a second shell and an air introduction unit. The first shell is provided apart from the housing and an envelope of the rotating-anode X-ray tube, and surrounds the envelope. The X-ray shielding member is provided between the first shell and the housing and apart from the housing. The second shell is provided apart from the housing to cause an airway to be formed between the second shell and the housing. The air introduction unit produces a flow of air in the airway.

17 Claims, 8 Drawing Sheets

(51) Int. Cl.
  *H05G 1/02* (2006.01)
  *H01J 35/10* (2006.01)
  *H01J 7/26* (2006.01)
  *H01J 19/36* (2006.01)
  *H01J 19/54* (2006.01)
  *H01J 19/74* (2006.01)
  *A61B 6/00* (2006.01)
  *A61B 6/10* (2006.01)
  *H01J 35/26* (2006.01)
  *H05G 1/04* (2006.01)

(52) U.S. Cl.
  CPC .............. *H01J 19/36* (2013.01); *H01J 19/54* (2013.01); *H01J 19/74* (2013.01); *H01J 35/16* (2013.01); *H01J 37/165* (2013.01); *H05G 1/025* (2013.01); *H01J 35/26* (2013.01); *H01J 2229/0061* (2013.01); *H01J 2229/863* (2013.01); *H01J 2229/8638* (2013.01); *H01J 2235/12* (2013.01); *H01J 2235/1216* (2013.01); *H01J 2235/166* (2013.01); *H01J 2237/002* (2013.01); *H01J 2237/16* (2013.01); *H05G 1/04* (2013.01)

(58) Field of Classification Search
  CPC .. H05G 1/02; H05G 1/025; H05G 1/04; H01J 7/00; H01J 7/24; H01J 7/26; H01J 19/00; H01J 19/36; H01J 19/40; H01J 19/54; H01J 19/56; H01J 19/74; H01J 29/00; H01J 29/06; H01J 29/006; H01J 29/86; H01J 29/861; H01J 29/867; H01J 29/868; H01J 35/00; H01J 35/02; H01J 35/105; H01J 35/106; H01J 35/16; H01J 37/00; H01J 37/02; H01J 37/09; H01J 37/16; H01J 37/165; H01J 2237/00; H01J 2237/002; H01J 2237/16; H01J 2229/00; H01J 2229/0007; H01J 2229/0061; H01J 2229/0069; H01J 2229/0076; H01J 2229/0084; H01J 2209/86; H01J 2209/863; H01J 2209/8631; H01J 2209/8632; H01J 2209/8638; H01J 2235/00; H01J 2235/12; H01J 2235/1204; H01J 2235/1208; H01J 2235/1212; H01J 2235/1216; H01J 2235/16; H01J 2235/165; H01J 2235/166; H01J 2235/168

See application file for complete search history.

(56) References Cited

FOREIGN PATENT DOCUMENTS

| | | |
|---|---|---|
| JP | 2-5300 U | 1/1990 |
| JP | 11-290305 A | 10/1999 |
| JP | 2000-048745 | 2/2000 |
| JP | 2002-25792 A | 1/2002 |
| JP | 2007-514287 A | 5/2007 |
| JP | 2009-238742 A | 10/2009 |
| JP | 2010-211939 | 9/2010 |
| JP | 2010-244940 | 10/2010 |
| JP | 2010-244941 | 10/2010 |
| JP | 2010-257900 | 11/2010 |
| JP | 2010-257902 | 11/2010 |
| JP | 2013-175356 A | 9/2013 |
| JP | 2013-229328 | 11/2013 |
| JP | 2015-32512 A | 2/2015 |

OTHER PUBLICATIONS

Combined Office Action and Search Report dated Jun. 1, 2016 in Chinese Patent Application No. 201410604346.2 (with English language translation and English translation of Categories of Cited Documents).

Office Action dated Jun. 27, 2017, in Japanese Patent Application No. 2013-229327 (with English-language translation).

* cited by examiner

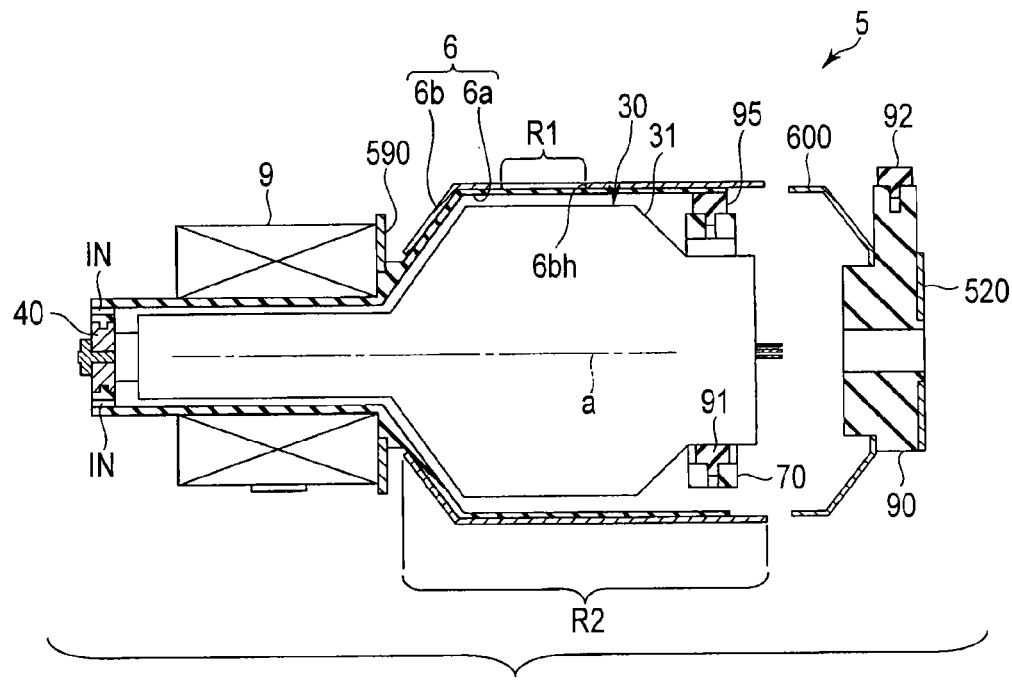
F I G. 2
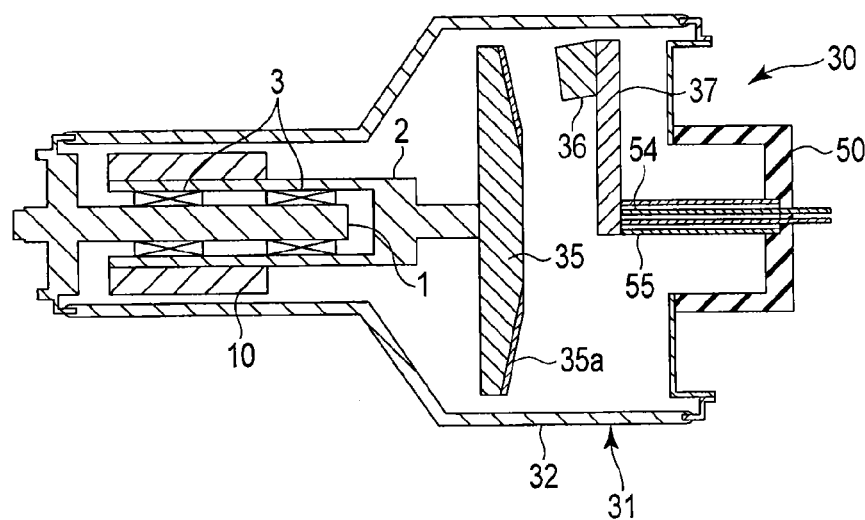
F I G. 3

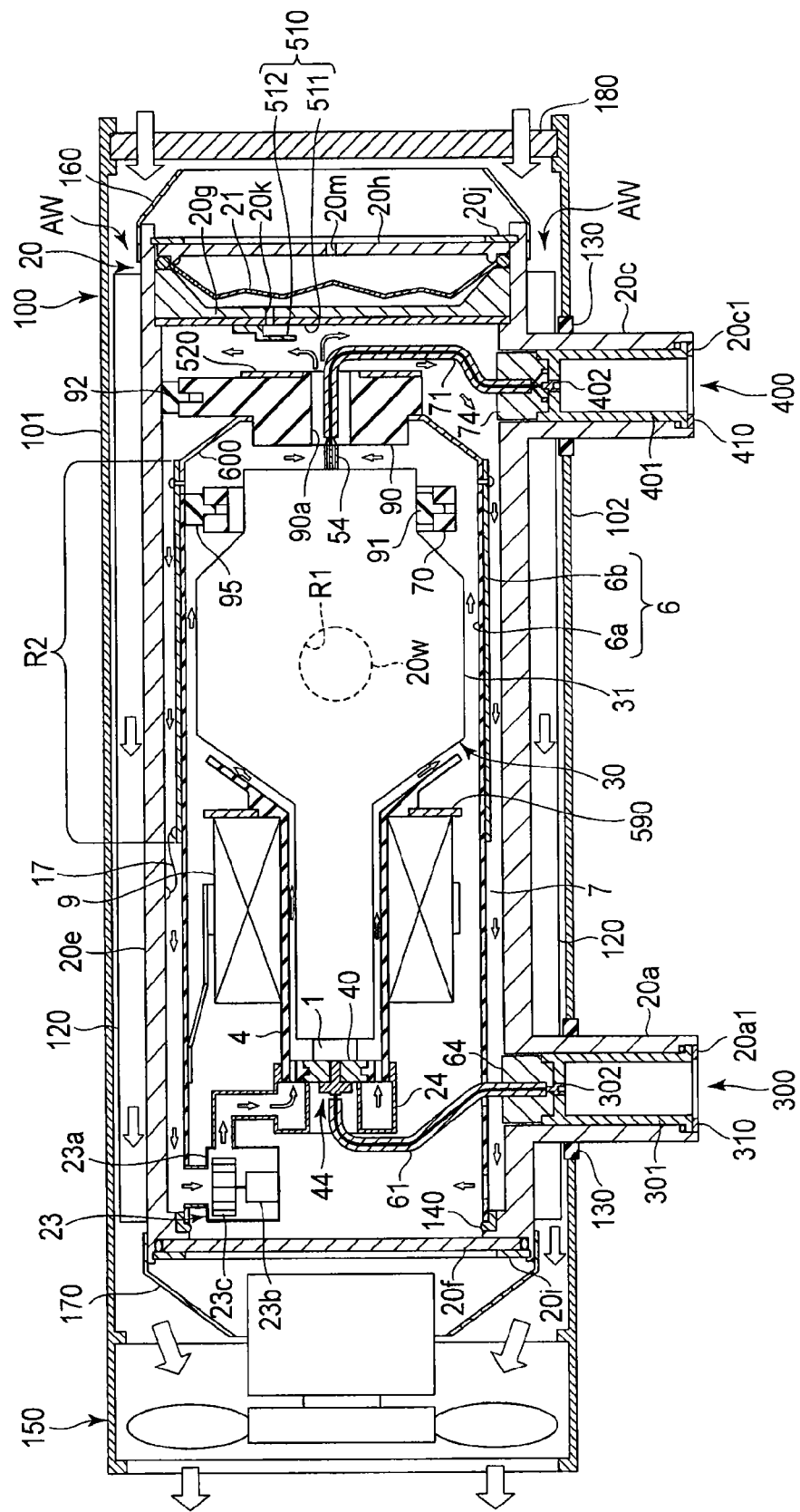
F I G. 5

ROTATING-ANODE X-RAY TUBE ASSEMBLY WITH COOLING SYSTEM

CROSS-REFERENCE TO RELATED APPLICATIONS

This application is based upon and claims the benefit of priority from Japanese Patent Application No. 2013-229327, filed Nov. 5, 2013, the entire contents of which are incorporated herein by reference.

FIELD

Embodiments described herein relate generally to a rotating-anode X-ray tube assembly.

BACKGROUND

In X-ray photography applied in a medical field, etc., in general, an X-ray apparatus is used which adopts a rotating-anode X-ray tube assembly as an X-ray source. As the X-ray photography, Roentgen photography and computerized tomography (CT) are applied. The rotating-anode X-ray tube assembly comprises a housing, a rotating-anode X-ray tube provided in the housing to radiate X-rays, and a coolant (insulating oil) filled between the housing and the rotating-anode X-ray tube.

The housing is formed of a brittle material such as a cast aluminum. To an inner surface of the housing, a lead plate is provided to prohibit stray X-rays from emanating out of the housing. Also, at the housing, an X-ray transmission window is provided.

The rotating-anode X-ray tube comprises an anode target, a cathode and an envelope which accommodates the anode target and the cathode, and which is evacuated. The anode target can be rotated at a high speed (e.g., 10,000 RPM). The anode target includes a target layer (umbrella portion) formed of a tungsten alloy. The cathode is located eccentric from an axis of the anode target and opposite to the target layer.

Between the cathode and the anode target, a high voltage is applied. Thus, when being ejected from the cathode, electrons are accelerated and converted to collide with the target layer. As a result, the target layer emits X-rays, which transmit from the X-ray transmission window to the outside of the housing.

There is a case where an X-ray tube assembly for use in an X-ray CT scanner or a cardio-vascular imaging system is required to radiate X-rays having a high intensity. Also, there is a case where the X-ray tube assembly is required to continuously radiate X-rays for a long time or radiate X-rays with a high repetition rate. In this case, since it is necessary to forcibly cool a coolant, the X-ray tube assembly is provided with a cooler unit.

The cooler unit is provided at part of a circulation path for the coolant, and is located outside the housing. The cooler unit comprises a heat exchanger, a conduit which is connected to the housing and the heat exchanger to form the circulation path for the coolant, and a circulation pump which circulates the coolant in the circulation path. In accordance with how heat transmitted from the coolant to the heat exchanger is dissipated, the cooler unit is broadly classified into an air-cooling type of cooler unit and a water-cooling type of cooler unit. The air-cooling type of cooler unit forcedly cools the heat transmitted from the coolant to the heat exchanger using forced air flow. The water-cooling type of cooler unit transmits the heat transmitted from the coolant to the heat exchanger to a water-based coolant having a lower temperature than the above former coolant. In this case, in order to dissipate the heat transmitted to the water-based coolant, an air-cooling type of cooler unit is provided in a circulation path for the water-based coolant.

BRIEF DESCRIPTION OF THE DRAWINGS

FIG. 2 is a cross-sectional view showing a rotating-anode X-ray tube unit of the first embodiment;

FIG. 3 is a cross-sectional view showing a rotating-anode X-ray tube of the first embodiment;

FIG. 5 is a cross-sectional view showing a rotating-anode X-ray tube assembly of a second embodiment;

DETAILED DESCRIPTION

In general, according to one embodiment, there is provided a rotating-anode X-ray tube assembly comprising: a rotating-anode X-ray tube comprising a cathode which configured to emit electrons, an anode target configured to emit X rays, a supporting mechanism which supports the anode target in such a way as to allow the anode target to be rotated, and an envelope which accommodates the cathode, the anode target and the supporting mechanism; a housing which accommodates the rotating-anode X-ray tube; a coolant filled in space between the rotating-anode X-ray tube and the housing; a first shell provided between the envelope and the housing and apart from the envelope and the housing, extending along an axis of the anode target, and surrounding the envelope; an X-ray shielding member provided between the first shell and the housing and apart from the housing, and including a through hole through which the X rays are made to pass; a second shell provided apart from the housing, surrounding the housing in a direction perpendicular to the axis, and forming an airway between the second shell and the housing; and an air introduction unit configured to introduce air into the airway to produce a flow of air.

Figure 1:
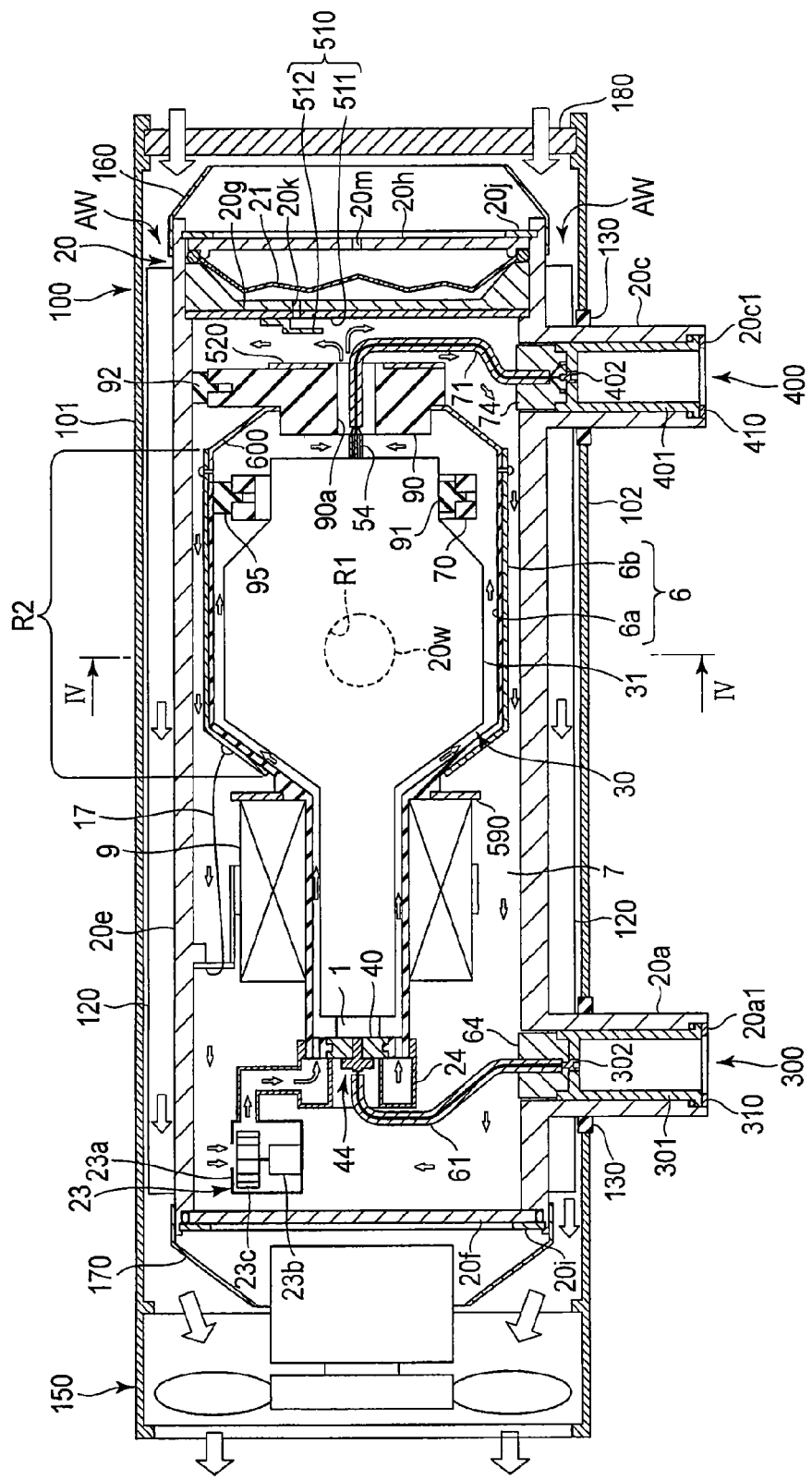
FIG. 1 is a cross-sectional view showing a rotating-anode X-ray tube assembly of a first embodiment.

A rotating-anode X-ray tube assembly of a first embodiment will be explained in detail with reference to the accompanying drawings. FIG. 1 is a cross-sectional view showing the X-ray tube assembly of the first embodiment. FIG. 2 is a cross-sectional view showing a rotating-anode X-ray tube unit of the first embodiment. FIG. 3 is a cross-sectional view showing a rotating-anode X-ray tube of the first embodiment.

As shown in FIG. 1, broadly speaking, the X-ray tube assembly comprises: a housing 20; a rotating-anode X-ray tube 30 provided in the housing 20; a coolant 7 filled as a cooling medium in space between the X-ray tube 30 and the housing 20; a shield structure 6; a stator coil 9 serving as a rotary drive module; a circulation unit 23; high-voltage cables 61 and 71; receptacles 300 and 400; a shell 100; an air induction unit 150; and an air filter 180.

The housing 20 includes a cylindrical main body 20e and lid portions (side plates) 20f, 20g and 20h. The main body 20e and the lid portions 20f, 20g and 20h are formed of metal material and/or resin material. Although it will be described later, the main body 20e of the first embodiment functions as a radiator, and it is therefore preferable that the main body 20e be formed of material having a high thermal conductivity, such as metal. It should be noted that if the main body 20e is formed of metal material, heat of the coolant 7 is easily transmitted to the main body 20e and easily dissipated to the outside, as compared with the case where the main body 20e is formed of resin material.

In the first embodiment, the main body 20e and the lid portions 20f, 20g and 20h are formed of a cast aluminum. If resin material is applied as material of the main body 20e and the lid portions 20f, 20g and 20h, metal may also be applied as material of part of the above portions; i.e., for example, the following portions may be formed of metal: a portion which needs to have an enough strength, such as a screw portion; a portion which cannot be easily formed by injection molding of resin, and a shielding layer not shown which prevents leakage of an electromagnetic noise from the housing 20 to the outside thereof.

Also, if the housing 20 is formed of resin material, it is preferable that the resin material contain at least one of thermosetting epoxy resin, unsaturated polyester resin, phenol resin, diallyl phthalate resin, thermoplastic epoxy resin, nylon resin, aromatic nylon resin, polybutylene terephthalate resin, polyethylene terephthalate resin, polycarbonate resin, polphenylene sulfide resin, polyphenylene ether resin, liquid crystal polymer, and methylpentene polymer.

An annular step portion is formed in an opening portion of part of the main body 20e, in which a high-voltage supplying terminal 44 to be described later is located. Also, an annular groove portion is formed in an inner peripheral surface of the above step portion. In a direction along a tube axis of the X-ray tube assembly, a peripheral edge portion of the lid portion 20f is in contact with the step portion of the main body 20e. In the groove portion of the main body 20e, a C-type snap ring 20i is fitted.

The C-type snap ring 20i restricts the position of the lid portion 20f with respect to the main body 20e in the direction along the tube axis. In the first embodiment, in order to prevent the lid portion 20f from shaking, the lid portion 20f is fixed in position. In a direction perpendicular to the tube axis, a gap between the main body 20e and the lid portion 20f is liquid-tightly sealed with an O-ring. The O-ring has a function of preventing leakage of the coolant 7 from the housing 20 to the outside thereof. The O-ring is formed of resin or rubber.

Due to the above structure, the opening portion of the part of the main body 20e, in which the high-voltage supplying terminal 44 is located, is liquid-tightly closed by the lid portion 20f, the C-type snap ring 20i and the O-ring.

An annular step portion is formed in an opening portion of part of the main body 20e, in which a high-voltage supplying terminal 54 to be described later is located. In an inner peripheral surface of the step portion, an annular groove portion is formed. The lid portion 20g is located in the main body 20e. In the direction along the tube axis, a peripheral edge of the lid portion 20g holds along with the step portion of the main body 20e, an X-ray shielding member 510 to be described later. The lid portion 20h is located opposite to the lid portion 20g. In the first embodiment, the lid portion 20h includes an annular portion, which is formed to project toward the lid portion 20g.

Gaps among the inner peripheral surface of the main body 20e, the lid portion 20g and the lid portion 20h are liquid-tightly sealed by a frame-shaped O-ring. The O-ring corresponds to a peripheral edge portion of a rubber bellows 21, and has a function of preventing leakage of the coolant 7 from the housing 20 to the outside thereof.

In the groove portion of the main body 20e, the C-type snap ring 20j is fitted. The C-type snap ring 20j holds the lid portion 20h applying a stress on the 0-ring. Due to such a structure, the opening portion of the part of the main body 20e, in which the high-voltage supplying terminal 54 is located, is liquid-tightly closed by the lid portion 20g, the lid portion 20h, the C-type snap ring 20j and the rubber bellows 21.

The lid portion 20g includes an opening portion 20k for entrance and exit of the coolant 7. The lid portion 20h includes an air hole 20m for entrance of exit of air which is used as an atmosphere. In the housing 20, the rubber bellows 21 partitions a space surrounded by the lid portion 20g and the lid portion 20h into a first space communicating with the opening portion 20k and a second space communicating with the air hole 20m. The pressure of the coolant 7 is adjusted by the rubber bellows 21.

Figure 4:
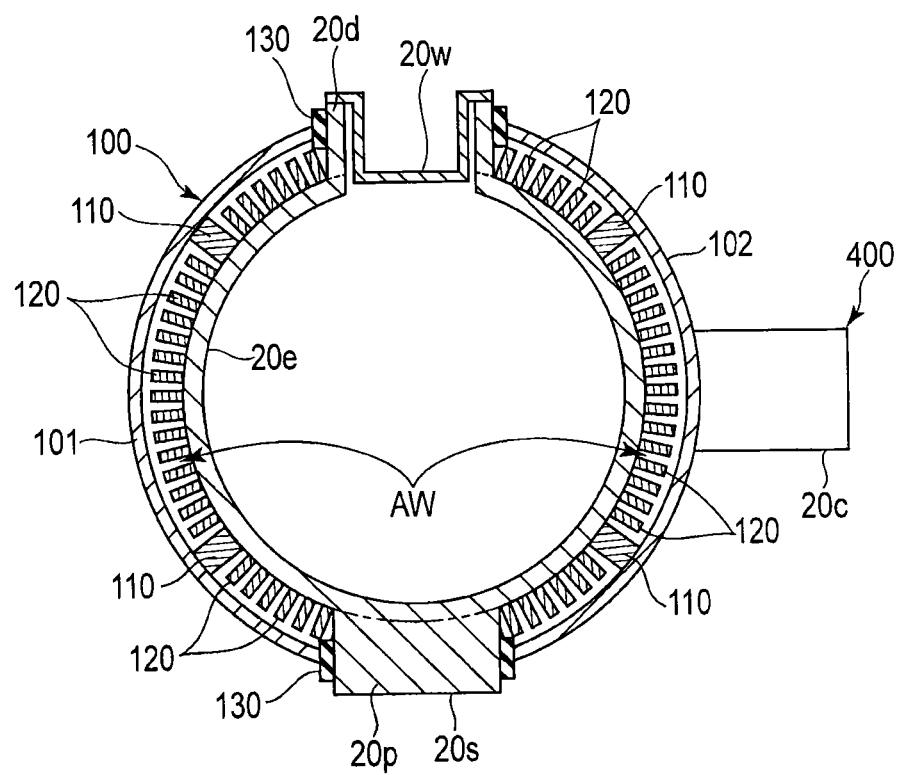
FIG. 4 is a cross-sectional view showing the rotating-anode X-ray tube assembly of the first embodiment, which is taken along line IV-IV in FIG. 1, and only showing a housing, a shell, a plurality of spacers, a plurality of fins, a rubber member and an X-ray transmission window (The rotating-anode X-ray tube, a first shell, and an X-ray shielding member are not shown.)

FIG. 4 is a cross-sectional view showing the X-ray tube assembly, which is taken along line IV-IV in FIG. 1. It shows only the housing 20, the shell 100, a plurality of spacers 110, a plurality of radiating fins 120, a rubber member 130 and an X-ray transmission window 20w. (The rotating-anode X-ray tube, a first shell, and an X-ray shielding member are not shown.)

As shown in FIGS. 1 and 4, the housing 20 includes the X-ray transmission window 20w, which is located opposite to an X-ray transmission region R1. The X-ray transmission window 20w liquid-tightly closes along with an O-ring not shown, an X-ray transmission port formed in a frame portion 20d of the housing 20. The X-ray transmission window 20w can be formed of material having a high mechanical strength. In the first embodiment, the X-ray transmission window 20w is formed of aluminum; however, it can be formed of other metal material, resin or the like. The X-ray transmission window 20w permits X-rays to pass therethrough, and thus emits the rays to the outside of the housing 20. It should be noted that to an inner surface of the housing 20, a lead plate is not bonded.

As shown in FIGS. 1-3, the X-ray tube 30 comprises an envelope 31, an anode target 35 and a cathode 36. The envelope 31 includes a large-diameter portion, a small-diameter portion and an intermediary portion. The large-diameter portion is located opposite to the anode target 35 in a direction perpendicular to an axis a to be described later. The small-diameter portion is located opposite to a rotor 10 to be described later in the direction perpendicular to the axis a. The intermediary portion connects the large-diameter portion and the small-diameter portion.

The envelope 31 includes a container 32 as the large-diameter portion. The container 32 is formed of, e.g., glass or metal such as copper, stainless or aluminum. In the first embodiment, the container 32 is formed of glass. It should be noted that if the container 32 is formed of metal, it includes an opening located opposite to the X-ray transmission region R1. The opening of the container 32 is vacuum-tightly closed by an X-ray transmission window formed of beryllium which is material allowing X-rays to be transmitted therethough. Part of the envelope 31 is formed of a high-voltage insulating member 50. In the first embodiment, the high-voltage insulating member 50 is formed of glass.

The anode target 35 is provided in the envelope 31. Also, the anode target 35 is formed discoid, and includes a target layer 35a formed in the shape of an umbrella and provided at part of an outer surface of the anode target. The target layer 35a emits X-rays when electrons emitted from the cathode 36 collide with the target layer 35a. The anode target 35 is formed of metal such as molybdenum.

An outer side surface of the anode target 35 and a surface of the anode target 35, which is located opposite to the target layer 35a, are subjected to blacking processing. The target layer 35a is formed of metal such as molybdenum, a molybdenum alloy or a tungsten alloy. The anode target 35 is rotatable around the tube axis. Thus, the axis a of the anode target 35 is parallel to the tube axis.

The cathode 36 is provided in the envelope 31. Also, the cathode 36 emits electrodes which are to collide with the anode target 35. A Kovar (KOV) member 55, which is a low-expansion alloy, is provided to cover the high-voltage supplying terminal 54 in the envelope 31. In this case, the gap between the high-voltage supplying terminal 54 and the high-voltage insulating member 50 is sealed with glass, and the KOV member 55 is fixed to the high-voltage insulating member 50 by a friction fit. To the KOV member 55, a cathode supporting member 37 is attached. The cathode 36 is attached to the cathode supporting member 37.

The high-voltage supplying terminal 54 is connected to the cathode 36 through the cathode supporting member 37.

The X-ray tube 30 comprises a fixed shaft 1, a rotating body 2, a bearing 3 and the rotor 10. The fixed shaft 1 is cylindrically formed. At part of an outer peripheral of the fixed shaft 1, a projection portion is formed, and vacuum-tightly attached to the envelope 31. Also, to the fixed shaft 1, the high-voltage supplying terminal 44 is electrically connected. The fixed shaft 1 supports the rotating body 2 to allow the rotating body 2 to be rotated. The rotating body 2 is cylindrically formed, and provided coaxial with the fixed shaft 1. To an outer surface of the rotating body 2, the rotor 10 is attached. Also, to the rotating body 2, the anode target 35 is attached. The bearing 3 is provided between the fixed shaft 1 and the rotating body 2. The rotating body 2 is supported by the bearing 3 in such a way as to be rotatable around the fixed shaft 1. The rotating body 2 is provided rotatable along with the anode target 35. The fixed shaft 1, the rotating body 2 and the bearing 3 form a supporting mechanism which supports the anode target 35 in such a way as to allow the anode target 35 to be rotated.

The high-voltage supplying terminal 44 applies a voltage to the anode target 35 through the fixed shaft 1, the bearing 3 and the rotating body 2. The high-voltage supplying terminal 54 applies a voltage to the cathode 36, and supplies a filament current to a filament (electron emission source) of the cathode 36, which is not shown. Since an X-ray tube voltage is applied between the anode target 35 and the cathode 36, a potential of the anode target 35 is set higher than that of the cathode 36.

In the first embodiment, the high-voltage supplying terminal 44 and the high-voltage supplying terminal 54 are metallic terminals. To the anode target 35, a positive voltage is applied, and to the cathode 36, a negative voltage is applied.

Furthermore, the X-ray shielding member 510 is provided on one end portion of the housing 20, which is located opposite to the target layer 35a in the direction along the axis a. The X-ray shielding member 510 serves as a shield against X-rays radiated from the target layer 35a. The X-ray shielding member 510 is formed of material containing an X-ray impermeable material. The X-ray shielding member 510 includes a first shielding member 511 and a second shielding member 512.

The first shielding member 511 is bonded to part of the lid portion 20g, which is located opposite to the target layer 35a in the direction along the axis a. The first shielding member 511 covers the entire lid portion 20g. Also, at part of the first shielding member 511, which is located opposite to the opening portion 20k, an opening is formed to communicate with the opening portion 20k, thus ensuring entrance and exist of the coolant 7. The second shielding member 512 is provided on the first shielding member 511. Also, the second shielding member 512 serves as a shield against X-rays which may be emitted from the vicinity of the opening portion 20k to the outside of the housing 20.

A fixing member 90 is provided in the housing 20. Also, on a side located opposite to the anode target 35 with respect to the cathode 36, the fixing member 90 is located outward of the X-ray tube 30. The fixing member 90 fixes the X-ray tube 30 in position with respect to the housing 20. The fixing member 90 is an electrical insulating member, and also formed of an electrical insulating material such as resin.

The fixing member 90 itself is fixed to the housing 20. To be more specific, it is fixed to the housing 20 by a plurality of rubber members (electrical insulating members) 92. For example, in three or four positions, the fixing member 90 is fixed along with the rubber members 92 to the housing 20. The rubber members 92 are in contact with the housing 20. Thus, the fixing member 90 and the rubber members 92 are fixed to the housing 20 by a friction fit.

In the fixing member 90, a through hole 90a is formed. The through hole 90a is used as a space for connection between the high-voltage supplying terminal 54 and a high-voltage cable 71, a passage for the high-voltage cable 71 and a flow pass for the coolant 7.

To the fixing member 90, a X-ray shielding member 600 and an X-ray shielding member 520 are attached. The X-ray shielding member 600 is formed of a hard lead. Also, the X-ray shielding member 600 is formed in the shape of a frame, and contributes to shielding against undesired X-rays (e.g., scattered X-rays).

The X-ray shielding member 520 is attached to part of the fixing member 90, which is located opposite to the X-ray shielding member 510 in the direction along the axis a. Also, an opening is formed in part of the X-ray shielding member 520, which is located opposite to the through hole 90a. The X-ray shielding members 510 and 520 are grounded.

Furthermore, as described above, in a combined structure of the fixing member 90, the X-ray shielding member 520 and the X-ray shielding member 600, lead and insulating material are applied in combination. Thus, the quantity of lead to be applied can be reduced. Also, it can be ensured that the high-voltage cable 71, the X-ray shielding member 600 and the X-ray shielding member 520 are insulated from each other.

The shield structure 6 surrounds an entire vacuum space of the envelope 31 in the direction perpendicular to the axis a. The shield structure 6 includes the X-ray transmission region R1 and an X-ray shield region R2 surrounding the X-ray transmission region R1. The X-ray transmission region R1 permits X-rays to be transmitted therethrough, and the X-ray shield region R2 serves as a shield against X-rays.

The shield structure 6 includes an insulating member 6a serving as a first shell and an X-ray shielding member 6b. A flow-path formation member formed of the insulating member 6a forms a flow path for the coolant 7, which is located between the flow-path formation member and the envelope 31. A flow-path formation member formed of the insulating member 6a and the X-ray shielding member 6b forms another flow path for the coolant 7, which is located between the flow-path formation member and the housing 20.

The insulating member 6a is formed of an electrical insulating material. The insulating member 6a is located between the envelope 31 and the housing 20. Also, the insulating member 6a is separated from the envelope 31 and the housing 20 by respective distances in the direction perpendicular to the axis a. The insulating member 6a surrounds the envelope 31 (the entire vacuum space of the envelope 31) in the direction perpendicular to the axis a. The insulating member 6a extends in the direction along the axis a, and is tubularly shaped. The insulating member 6a is shaped in accordance with the shape of the X-ray tube 30. The diameter of the insulating member 6a varies along the axis a. The insulating member 6a electrically insulates between the X-ray tube 30 and the housing 20, and between the X-ray tube 30 and the stator coil 9.

The insulating member 6a is formed of a resin material which contains at least one of thermosetting epoxy resin, unsaturated polyester resin, phenol resin, diallyl phthalate resin, thermoplastic epoxy resin, nylon resin, aromatic nylon resin, polybutylene terephthalate resin, polyethylene terephthalate resin, polycarbonate resin, polphenylene sulfide resin, polyphenylene ether resin, liquid crystal polymer and methylpentene polymer. According to some circumstances and conditions, the insulating member 6a functions as a protection member.

It should be noted that the insulating member 6a may be formed such that the insulating member 6a and the X-ray shielding member 6b are provided as a single body. Also, it is possible to replace the insulating member 6a with a metallic member.

The insulating member 6a (the shield structure 6) is fixed to the X-ray tube 30 by a connection member 40. The insulating member 6a and the connection member 40 are mechanically firmly fixed to each other. The connection member 40 is formed of brass or the like, and can be formed such that the connection member 40 and the insulating member 6a are provided as a single body by an injection molding method. The insulating member 6a includes a plurality of intakes IN for taking in the coolant 7. The insulating member 6a forms an outlet for taking out the coolant 7, which is located between the insulating member 6a and the envelope 31.

The X-ray shielding member 6b is located between the insulating member 6a and the housing 20. The X-ray shielding member 6b is provided apart from the housing 20 in the direction perpendicular to the axis a. The X-ray shielding member 6b is also provided in the X-ray shield region R2, and serves as a shield against X-rays. Furthermore, the X-ray shielding member 6b includes a through hole 6bh corresponding to the X-ray transmission region R1. For example, the through hole 6bh is circular. Also, the through hole 6bh serves as a X-ray transmission port. The X-ray shielding member 6b is cylindrically formed.

The X-ray shielding member 6b is fixed to the insulating member 6a. Also, the X-ray shielding member 6b is formed to be in tight contact with or close vicinity to the insulating member 6a. In the first embodiment, the X-ray shielding member 6b is formed to be in tight contact with the insulating member 6a. Also, the X-ray shielding member 6b is bonded to the insulating member 6a.

The X-ray shielding member 6b is electrically connected to the main body 20e, which is formed of a conductor. It is also grounded. In the first embodiment, the X-ray shielding member 6b is electrically connected to the housing 20 by a conductor (grounding conductor) 17 and a fixing fitting for the stator coil 9. Therefore, it is possible to stabilize the potential of the X-ray shielding member 6b. Also, it is possible to prevent induction of discharge of electricity from the X-ray tube 30 in the case where the X-ray shielding member 6b is in an electrically floating state.

At an end portion of the X-ray shielding member 6b, the X-ray shielding member 6b overlaps the X-ray shielding member 600 in the direction perpendicular to the axis a. The inside diameter of the end portion of the X-ray shielding member 6b is slightly greater than the outside diameter of an end portion of the X-ray shielding member 600. The X-ray shielding member 6b and the X-ray shielding member 600 are joined to each other by a screw 18b.

Thus, the X-ray shielding member 600 serves as an X-ray shield which covers along with the X-ray shielding member 510 and the X-ray shielding member 520, the opening of the X-ray shielding member 6b. The X-ray shielding member 6b, the X-ray shielding member 510, the X-ray shielding member 520 and an X-ray shielding member 590 can block X rays radiated to the outside of the X-ray transmission region R1, thus preventing leakage of the X-rays from the housing 20 to the outside thereof.

It should be noted that the X-ray shielding member 590 is annularly formed. The X-ray shielding member 590 is attached to the stator coil 9, and also set to have the same potential as the housing 20. The X-ray shielding member 590 contributes to shielding against scattered X rays.

Furthermore, the X-ray shielding member 6b extends from a position where it is located opposite to the X-ray shielding member 600 along the axis a, to a position where it is located outward of the anode target 35 (on a line extending from a surface of the target layer 35a). In the first embodiment, the X-ray shielding member 6b extends from the position where it is located opposite to the X-ray shielding member 600 to a position just prior to the stator coil 9.

The X-ray shielding member 6b is formed of a hard lead. Also, the X-ray shielding member 6b has a thickness of approximately 1 to 5 mm. This thickness means a wall thickness of the X-ray shielding member 6b, and that in the first embodiment corresponds to the shortest distance between the inner peripheral surface and outer peripheral surface of the X-ray shielding member 6b in the direction perpendicular to the axis a.

The X-ray shielding member 6b may be formed of material containing an X-ray impermeable material. As the X-ray impermeable material applied to the X-ray shielding member 6b, etc., metal including at least one of tungsten, tantalum, molybdenum, barium, bismuth, rare-earth metal and lead, and a compound of at least one of tungsten, tantalum, molybdenum, barium, bismuth, rare-earth metal and lead can be used.

Surfaces of the X-ray shielding member 6b, the X-ray shielding member 510, the X-ray shielding member 520, the X-ray shielding member 590 and the X-ray shielding member 600, the surfaces may be plated with metal such as tin, silver, copper or nickel, or may be coated with resin, in order to protect them against corrosion.

If the shield structure 6 has a certain strength and ductility, and surrounds the entire anode target 35, it can function as a protection body. For example, the insulating member 6a can function as a protection body by itself. If the anode target 35 is broken during a high-speed rotating operation, fragments of the anode target 35, which have a high kinetic energy, breaks the container 32 formed of glass, and further fly apart toward the inner surface of the housing 20. The shield structure 6 protects the housing 20 from the fragments having a high kinetic energy which fly apart from the anode target 35.

Even if the fragments of the anode target 35 collide with the shield structure 6, the shield structure 6 is sufficiently deformed and can thus absorb the kinetic energy of the fragments. In such a manner, even if the shield structure 6 is sufficiently deformed, the housing 20 itself can be prevented from being deformed, since the shield structure 6 and the housing 20 are located apart from each other. It is therefore possible to prevent generation of a crack or cracks in the housing 20, which would be generated if the above feature is absent.

An annular portion 70 is annularly formed, and provided around the large-diameter portion of the X-ray tube 30 (the envelope 31) and apart from the large-diameter portion. The annular portion 70 is formed of electrical insulating material such as resin. A plurality of rubber members (electrical insulating members) 91 are attached to an inner peripheral surface side of the annular portion 70, and are also in contact with the large-diameter portion of the X-ray tube 30 (the envelope 31). Furthermore, a plurality of rubber members (electrical insulating members) 95 are attached to an outer peripheral surface side of the annular portion 70, and are also in contact with the insulating member 6a. Thus, the annular portion 70 and the rubber members 91 and 95 fix the X-ray tube 30 to the shield structure 6 due to a friction fit.

At least the X-ray tube 30, the shield structure 6, the annular portion 70, the fixing member 90, the X-ray shielding member 600, the X-ray shielding member 520 and the rubber members 91, 92 and 95 form a rotating-anode X-ray tube unit 5. In the first embodiment, the X-ray tube unit 5 is formed by adding the connection member 40, the stator coil 9 and the X-ray shielding member 590 to the X-ray tube 30, the shield structure 6, the annular portion 70, the fixing member 90, the X-ray shielding member 600, the X-ray shielding member 520 and the rubber members 91, 92 and 95.

As shown in FIG. 1, the stator coil 9 is fixed to a plurality of portions of the housing 20. Also, the stator coil 9 is located opposite to the X-ray tube 30 with respect to the shield structure 6, and surrounds an outer side of the envelope 31 such that it is located opposite to an outer surface of the rotor 10. The stator coil 9 restricts the position of the shield structure 6 in the direction perpendicular to the axis a. In the first embodiment, the stator coil 9 is in contact with an outer surface of the insulating member 6a. It should be noted that in order to prevent the X-ray tube 30 from shaking, part of the stator coil 9 is adhered to the outer surface of the insulating member 6a by an adhesive.

The stator coil 9 is intended to rotate the rotor 10, the rotating body 2 and the anode target 35. When being supplied with a predetermined current, the stator coil 9 generates a magnetic field to be applied to the rotor 10, and as a result the anode target 35, etc. are rotated at a predetermined speed.

The X-ray tube assembly comprises the circulation unit 23 and a hollow portion 24. The circulation unit 23 is provided in the housing 20, and causes a forced convection to occur in the housing 20. Also, the circulation unit 23 comprises a chamber 23a, a motor 23b and fins 23c. The chamber 23a includes an intake and an outlet for the coolant 7.

The motor 23b is attached to an inner wall of the chamber 23a. The fins 23c are attached to the motor 23b in the chamber 23a. When being given power by a power supply portion not shown, the motor 23b rotates the fins 23c. The circulation unit 23 discharges the coolant 7 taken in the chamber 23a through the intake to the outside of the chamber 23a through the outlet.

The hollow portion 24 includes a cylindrical inner peripheral wall, a cylindrical outer peripheral wall and annular end walls. One of the annular end walls liquid-tightly closes an end of each of the inner and outer peripheral walls, and the other liquid-tightly closes the other end of each of the inner and outer peripheral walls. In the first embodiment, the other end walls are formed of the connection member 40 and the insulating member 6a, and include a plurality of intakes IN. An opening formed in part of the outer peripheral wall liquid-tightly communicates with the outlet of the chamber 23a.

The hollow portion 24 serves as a flow path which connects the outlet of the chamber 23a and the intakes IN. Thus, from a small-diameter portion side of the envelope 31 to a large-diameter portion side thereof, the coolant 7 flows in an inner coolant flow-path between a flow-path formation body (the insulating member 6a) and the envelope 31. Furthermore, after passing through the through hole 90a, the coolant 7 oppositely flows in an outer coolant flow-path between the flow-path formation body (the insulating member 6a and the X-ray shielding member 6b) and the housing 20. Thus, the circulation unit 23 causes the coolant 7 to flow in a fixed direction which is parallel to the axis a, in the coolant flow-path between the flow-path formation body (the insulating member 6a and the X-ray shielding member 6b) and the housing 20.

Since a forced convection can occur in the housing 20, the coolant 7 can be circulated in the housing 20. Thus, heat transmitted from the X-ray tube 30, etc. to the coolant 7 can be positively transmitted to the housing 20.

As the coolant 7, an water-based coolant or an insulating oil serving as an insulating coolant can be applied. In the first embodiment, the coolant 7 is an insulating oil.

The X-ray tube assembly includes a receptacle 300 for the anode and a receptacle 400 for the cathode. The receptacle 300 is located in a cylindrical portion 20a of the housing 20, and attached to the cylindrical portion 20a. The receptacle 400 is located in the cylindrical portion 20c of the housing 20, and attached to the cylindrical portion 20c. For example, the cylindrical portion 20a and the cylindrical portion 20c are formed integral with each other and of the same material as the main body 20e.

The receptacle 300 includes a housing 301 which is provided as an electrical insulating member, and a terminal 302 which is provided as a high-voltage supplying terminal.

The housing 301 is formed in the shape of a tub having an opening which is provided in an outer portion of the cylindrical portion 20a (the housing 20). The housing 301 is formed in the shape of a cup which is substantially axisymmetric. Furthermore, a plug-in of the housing 301 is open in an outer part of the housing 20.

At an end portion of an opening side of the housing 301, an annular projection portion is formed at an outer surface of the housing 301. The housing 301 is formed of an insulating material such as resin. The terminal 302 is liquid-tightly attached to a bottom portion of the housing 301, and penetrates the bottom portion.

A high-voltage cable 61 is immersed in the coolant 7. One of end portions of the high-voltage cable 61 is electrically connected to the high-voltage supplying terminal 44, and the other is electrically connected to the terminal 302 through space in the housing 20. The high-voltage, cable 61 and the high-voltage supplying terminal 44 can be connected to each other by welding or soldering. Alternatively, the high-voltage cable 61 and the high-voltage supplying terminal 44 can be detachably connected together by a friction fit.

An electrical insulating member 64 is formed of an electrical insulating material, filled in an electrical connection portion between the terminal 302 and the high-voltage cable 61, and directly adhered to the housing 301. To be more specific, the electrical insulating member 64 is formed of a mold material. Due to use of the electrical insulating member 64, it is possible to improve an electrical insulation between the housing 20 and an electrical connection portion between the terminal 302 and the high-voltage cable 61.

In addition to the above electrical connection portion, a mold material or the like is applied to another portion, thereby improving the electrical insulating characteristic of the inside of the housing 20. In this case, a water-based coolant can be applied as the coolant 7.

An O-ring is provided between the step portion of the cylindrical portion 20a and the projection portion of the housing 301. The step portion of the cylindrical portion 20a is subjected to internal thread processing. A ring nut 310 includes a side surface subjected to external thread processing. The ring nut 310 is tightened on the step portion of the cylindrical portion 20a, thus pressing the housing 301. The O-ring is pressurized by the step portion of the cylindrical portion 20a and the projection portion of the housing 301. The receptacle 300 is liquid-tightly attached to the cylindrical portion 20a, and can thus prevent leakage of the coolant 7 from the housing 20 to the outside thereof.

The receptacle 300 and a plug not shown, which is to be inserted thereinto, are of a non-contact pressure type in which the plug does not need to be tightly inserted into the receptacle 300, and are formed such that the plug can be inserted into and removed from the receptacle 300. A high voltage (e.g., +70 to +80 kV) is applied from the plug to the terminal 302, with the plug inserted in the receptacle 300.

The receptacle 400 is formed in the same manner as the receptacle 300.

The receptacle 400 includes a housing 401 which is provided as an electrical insulating member, and a terminal 402 which is provided as a high-voltage applying terminal.

The housing 401 is formed in the shape of a tub having an opening provided in an outer part of the cylindrical portion 20c (the housing 20). The housing 401 is formed in the shape of a cup which is substantially axisymmetric. Furthermore, a plug-in of the housing 401 is open in an outer part of the housing 20.

At an end portion of an opening side of the housing 401, an annular projection portion is formed in the outer surface of the housing 401. The housing 401 is formed of an insulating material such as resin. The terminal 402 is liquid-tightly attached to a bottom portion of the housing 401, and penetrates the bottom portion.

The high-voltage cable 71 is immersed in the coolant 7. One of end portions of the high-voltage cable 71 is electrically connected to the high-voltage supplying terminal 54, and the other is electrically connected to the terminal 402 through the space in the housing 20. The high-voltage cable 71 and the high-voltage supplying terminal 54 can be connected to each other by welding or soldering. Alternatively, the high-voltage cable 71 and the high-voltage supplying terminal 54 can be detachably connected together by a friction fit.

An electrical insulating member 74 is formed of electrical insulating resin, filled in an electrical connection portion between the terminal 402 and the high-voltage cable 71, and directly adhered to the housing 401. To be more specific, the electrical insulating member 74 is formed of a mold material. By virtue of use of the electrical insulating member 74, it is possible to improve an electrical insulation between the housing 20 and an electrical connection portion between the terminal 402 and the high-voltage cable 71.

An O-ring is provided between the step portion of the cylindrical portion 20c and the projection portion of the housing 401. The step portion of the cylindrical portion 20c is subjected to internal thread processing. A ring nut 410 includes a side surface subjected to external thread processing. The ring nut 410 is tightened to the step portion of the cylindrical portion 20c to press the housing 401. Thereby, the O-ring is pressurized by the step portion of the cylindrical portion 20c and the projection portion of the housing 401. The receptacle 400 is liquid-tightly attached to the cylindrical portion 20c, and can thus prevent leakage of the coolant 7 from the housing 20 to the outside thereof.

The receptacle 400 and a plug not shown, which is to be inserted into the receptacle 400, are of a non-contact pressure type in which the plug does not need to be tightly inserted into the receptacle 400, and are formed such that the plug can be inserted into and removed from the receptacle 400. A high voltage (e.g., −70 to −80 kV) is applied from the plug to the terminal 402, with the plug inserted in the receptacle 400.

In the X-ray tube assembly comprising the above structure, when a predetermined current is supplied to the stator coil 9, the rotor 10 is rotated, and the anode target 35 is rotated. Then, a predetermined high voltage is applied to the receptacles 300 and 400.

The high voltage applied to the receptacle 300 is given to the anode target 35 through the high-voltage cable 61, the high-voltage supplying terminal 44, the fixed shaft 1, a bearing 930 and the rotating body 2. The high voltage applied to the receptacle 400 is given to the cathode 36 through the high-voltage cable 71 and the high-voltage supplying terminal 54.

Thereby, electrons emitted from the cathode 36 collide with the target layer 35a of the anode target 35, and X rays are radiated from the anode target 35. The X rays are radiated to the outside of the housing 20 through the through hole 6bh and the X-ray transmission window 20w.

As shown in FIGS. 1 and 4, the shell 100, which serves as a second shell, is provided apart from the housing 2, and surrounds the housing 20 in the direction perpendicular to the axis a. The shell 100 and the housing 20 (the main body 20e) form an airway AW between them. In the first embodiment, the shell 100 is cylindrically formed to have end portions including vents on its both sides, and extends in parallel with the axis a. The shell 100 is formed of metal or resin such as polycarbonate or polybutylene terephthalate.

The shell 100 is separated from the housing 20 by a predetermined distance by the spacers 110. The spacers 110 are provided between the housing 20 and the shell 100, and hold the airway AW.

The spacers 110 are individually formed in the shape of a block or a pillar, and arranged in a circumferential direction of the housing 20 (the main body 20e), in such a way as to enable air to flow in the airway AW. Also, the spacers 110 are formed of elastomeric resin such as rubber or urethane foam. Thus, the spacers 110 can reduce transmission of vibration from the X-ray tube 30 to the shell 100.

The shell 100 covers the housing 20, with the cylindrical portion 20a, the cylindrical portion 20c, the frame portion 20d (the X-ray transmission window 20w) and a projection portion 20p of the housing 20 exposed. Thus, the shell 100 includes openings associated with the cylindrical portion 20a, the cylindrical portion 20c, the frame portion 20d and the projection portion 20p, respectively. It should be noted that the projection portion 20p includes an attachment surface 20s for the X-ray tube assembly.

Furthermore, the shell 100 is made up of a plurality of divided portions. For example, the divided portions are separated from each other in the direction perpendicular to the axis a. In the first embodiment, the shell 100 is made up of a first divided portion 101 and a second divided portion 102. That is, the shell 100 can be easily formed by combining the first divided portion 101 and the second divided portion 102 together.

Also, the shell 100 is fixed to the housing 20, with rubber members 130 interposed between them, the rubber members 130 serving as elastic bodies. In the first embodiment, the shell 100 is fixed to the cylindrical portion 20a, the cylindrical portion 20c, the frame portion 20d and the projection portion 20p, with the rubber members 130. It should be noted that as the elastic bodies, elastomeric resin such as rubber or urethane foam as in the rubber member 130 can be used. Thus, the rubber members 130 can reduce transmission of vibration from the X-ray tube 30 to the shell 100.

Furthermore, it is preferable that the rubber members 130 (elastic bodies) also function as sealing members in order to enhance the airtightness between the housing 20 and the opening of the shell 100. This is because if the rubber members also function as sealing members, they can prevent a disorder or deceleration of an air stream in the airway AW.

It should be noted that it is possible to reduce the amount of shielding material to be prepared in the housing 20, by adding shielding material which blocks X rays from the X-ray tube 30 to resin material of which the shell 100 is formed. For example, as the above shielding material, metal fine particles of one of tungsten, tantalum, molybdenum, barium, bismuth, rare-earth metal and lead and/or compound fine particles of one of tungsten, tantalum, molybdenum, barium, bismuth, rare-earth material and lead are applied.

Due to a cooling action of an air flow which will be described later, the temperature of an outer surface of the shell 100 does not easily rise, as compared with the outer surface of the housing 20. Therefore, for example, it is therefore possible to restrict suffering of an operator or the like from a burn when the operator or the like contacts the shell 100. Thus, it is possible to improve the safety of the X-ray tube assembly.

Furthermore, in the first embodiment, if the X-ray tube assembly is designed that the temperature of the surface of the shell 100, not that of the housing 20, does not exceed 80° C., it can conform to international safety standards. Thus, the X-ray tube assembly may be formed such that an interlock operates when the temperature of the surface of the housing 20 reaches a predetermined temperature higher than 80° C.

The air induction unit 150 introduces air into the airway AW, and produces a flow of air. In the first embodiment, the air induction unit 150 is attached to one end portion of the shell 100, and discharges air passing through the airway AW to the outside of the X-ray tube assembly (the shell 100). Also, the air induction unit 150 comprises a fan unit.

By virtue of the above structure, since the housing 20, which also functions as a radiator, can radiate heat of the coolant 7 to the outside of the housing 20, it can restrict rising of the temperatures of the housing 20 and the coolant 7. Also, rising of the temperature of the shell 100 is restricted.

Part of the housing of the air induction unit 150, which is exposed to the outside of the X-ray tube assembly (the shell 100), is breathable. In the first embodiment, the exposed part of the housing is formed of a mesh. It is therefore possible to restrict entrance of dust from the air induction unit 150 into the airway AW. Furthermore, in the housing, such a mesh part as described above can also be used as a cover for fan of the air induction unit 150. It can also prevent a finger of the operator or the like from contacting the fan of the air induction unit 150, thus improving the safety of the X-ray tube assembly.

The radiating fins 120 are located in the airway AW, and also on the outer surface of the housing 20. The total surface area of the housing 20 and the radiating fins 120 is greater than the surface area of the housing 20 in the case where the radiating fins 120 are not provided thereon, thus also increasing the total area of portions which are in contact with air. Thus, the cooling performance of the X-ray tube assembly can be improved.

In the first embodiment, the radiating fins 120 are formed of plate-like members parallel to the axis a. The radiating fins 120 are arranged apart from each other in the circumferential direction of the housing 20. The gap between any adjacent two of the radiating fins 120 serves as a flow pass of air. Also, the radiating fins 120 are separated from the shell 100.

Also, it is possible to form the radiating fins 120 by molding the housing 20 and the radiating fins 120 such that they are formed as a single body.

The air filter 180 is located on an air intake side of the X-ray tube assembly; that is, it is located on the windward side with respect to the airway AW. In the first embodiment, the air filter 180 is attached to the other end portion of the shell 100. The air filter 180 is intended to remove dust contained in air when the air passes through the air filter 180. In other words, the air filter 180 can prevent entrance of dust into the airway AW. Thus, the air induction unit 150 can introduce clean air which has passed through the air filter 180 into the airway AW, and produce a flow of air to pass through the airway AW.

By virtue of the above structure, it is possible to prevent accumulation of dust on the radiating fins 120, etc., since air from which dust is removed pass through the gaps (ventilation portions) between the radiating fins 120, etc. Also, the gaps (ventilation portions) between the radiating fins 120 can be made hard to be blocked. It is possible to prevent lowering of the quantity (volume) of air passing through the airway AW, and is thus possible to prevent lowering of the radiation function of the radiator.

It should be noted that the air filter 180 can detachably attached by itself to the shell 100, or the air filter 180 can be detachably attached to the shell 100 by using another element, which is attached to the air filter 180. Thereby, it is easy to replace the air filter 180 with a new one, and clean the X-ray tube assembly including the air filter 180.

The X-ray tube assembly further comprises a contraction guide 160 and a diffusion guide 170.

The contraction guide 160 is located windward with respect to the airway AW, and guides air to the airway AW.

The contraction guide 160 is tubularly formed, and includes a cylindrical portion and a conical portion. The cylindrical portion is attached to one end portion of the housing 20 (the main body 20e). In the first embodiment, the cylindrical portion surrounds an outer peripheral surface of the one end portion, and is air-tightly attached to the one end portion. The conical portion is formed integral with the cylindrical portion. The gap between the shell 100 and an end portion of the conical portion, which is close to the cylindrical portion, is smaller than that between the shell 100 and another end portion of the conical portion, which is close to the air filter 180.

The contraction guide 160 can reduce the diameter of an air flow, and can thus compress an air flow located windward with respect to the airway AW to increase the velocity of wind in the airway AW. Thereby, a cooling effect can be enhanced. Furthermore, on a windward side with respect to the airway AW, the distribution of the wind velocity can be made uniform, and the disturbance of the air flow can be reduced. It should be noted that as the disturbance of the air flow reduces, the noise of wind also reduces.

The diffusion guide 170 is located leeward with respect to the airway AW, and guides air which has passed through the airway AW. The diffusion guide 170 is tubularly formed, and includes a cylinder portion and a conical portion. The cylinder portion is attached to another end portion of the housing 20 (the main body 20e). In the first embodiment, the cylinder portion surrounds an outer peripheral surface of the other end portion, and is air-tightly attached to the other end portion. The conical portion is formed integral with the cylinder portion. The gap between the shell 100 and an end portion of the conical portion, which is close to the cylindrical portion, is smaller than that between the shell 100 and another end portion of the conical portion, which is close to the air induction unit 150.

The diffusion guide 170 can increase the diameter of an air flow; and can thus diffuse the air flow, and increase the velocity of air in the airway AW. Thus, the cooling effect can be enhanced. Furthermore, the diffusion guide 170 can reduce the velocity of the air flow which has passed through the airway AW, and also reduce the noise of wind.

For example, the rotating-anode X-ray tube assembly according to the first embodiment and comprising the above structure can obtain the following advantages:

(1) The rotating-anode X-ray tube assembly can be made smaller.

To be more specific, as described above, it is possible to make the housing 20 (the main body 20e) itself function as a radiator. It should be noted that due to the air induction unit 150, a flow of air can be produced over a surface of the housing 20. Also, the X-ray tube assembly can be formed without preparing a radiator having a great surface area as an additional component.

(2) The rotating-anode X-ray tube assembly can ensure safety since it is designed in consideration of the contact of the X-ray tube assembly with a person.

To be more specific, an airway for outside air is provided on an outer periphery of the housing 20; and an exposed surface of the X-ray tube assembly is an outer surface of the shell 100, not that of the housing 20. Thus, even if the temperature of the housing 20 is high, since that of the shell 100 is low, a person can be prevented from suffering a burn even if the person touches the shell 100.

(3) Usage of X-ray shield material (lead) can be reduced, and X-ray shielding members can be easily removed in disassemblying processing.

The X-ray tube assembly comprises the shield structure 6 (X-ray shielding member 6b), the X-ray shielding member 510, the X-ray shielding member 520, the X-ray shielding member 590 and the X-ray shielding member 600. After being formed outside the housing 20, the X-ray shielding member 6b, etc. are incorporated into the housing 20. In the first embodiment, a lead plate does not need to be bonded to the inner surface of the housing 20, and the X-ray shielding member 6b, etc. can be easily manufactured, as compared with the case where the lead plate is bonded to the inner surface of the housing 20. Thereby, the manufacturing cost of the rotating-anode X-ray tube assembly can be reduced. Furthermore, lead can be easily separated from the main body 20e of the housing 20, as compared with the case where lead bonded to the inner surface of the housing is removed therefrom; and the lead can thus be effectively re-applied as resources.

Furthermore, since the X-ray shielding member 6b can be formed to have a smaller size (diameter), usage of lead can be decreased, and the rotating-anode X-ray tube assembly can be made lighter. Furthermore, the accuracy of shielding against X-rays can be increased. This is because unlike the first embodiment, if a lead plate is bonded to the inner surface of the housing 20, X rays can leak from the gap between the lead plates. Therefore, in the first embodiment, in the case where the X-ray tube assembly is mounted on an apparatus for medical diagnosis, it can prevent unnecessary radiation of X rays on the body of a person (prevent the person from getting exposed to radiation of X-rays).

(4) It is possible to ensure safety even if the anode target 35 is broken.

In the X-ray tube assembly, if the anode target 35 should be broken during a high-speed rotating operation, there would be a risk that fragments of the anode target 35 would fly apart, while having a high kinetic energy. If fragments of the anode target 35 fly apart, they break the envelope 31. Also, they collide with the housing 20 (formed of an aluminum casting), and thus may also break it (brittle fracture). In addition, the shell 100 can be broken. If the housing 20, etc. are broken during X-ray imaging, there is a risk that while having a high temperature, the coolant 7 will fly on an object to be examined (e.g., the body of a person).

In the case where the shield structure 6 has a certain strength and ductility, it can function as a protection member. To be more specific, if the anode target 35 is broken during the high-seed rotating operation, the shield structure 6 protects the housing 20 against fragments of the anode target 35, which fly while having a high kinetic energy. Even if the fragments of the anode target 35 collide with the shield structure 6, the shield structure 6 is sufficiently deformed, and can thus absorb the high kinetic energy of the fragments.

By virtue of the above structural feature, it is possible to prevent the housing 20 from being cracked. For example, in the case where the X-ray tube assembly is mounted on an apparatus for medical diagnosis, it is possible to eliminate the risk that the coolant 7 having a high temperature will fly on an object to be examined (e.g., the body of a person).

Furthermore, in the case where the shield structure 6 functions as a protection member, the housing 20 can be formed of resin material. Although the resin material has a lower heat-transfer coefficient and a lower mechanical strength than those of metal, it is inexpensive. Thus, the manufacturing cost and weight of the housing 20 can be decreased.

(5) Due to formation of the X-ray tube unit 5, the following advantages can be obtained:

With the X-ray tube unit 5 alone, it is possible to conduct a confirmation test to confirm whether or not X rays leak from part of the shield structure 6, which is other than the through hole 6bh. In the first embodiment, the shield structure 6 includes the insulating member 6a, and it is therefore further possible to conduct a confirmation test with the X-ray tube unit alone to check durability thereof against voltage; a reliability test can be conducted with the X-ray tube unit 5 alone, i.e., without the need to incorporate the X-ray tube unit 5 into the X-ray tube assembly; and a transportation cost can be reduced, since X-ray tube units 5 can be transported without the need to incorporate them into X-ray tube assemblies.

(6) Due to provision of the shield structure 6, the following advantages can be obtained:

The insulating member 6a surrounds the X-ray tube 30, and is superior to the coolant 7 in insulating characteristic. Due to provision of the insulating member 6a, an insulating pass between the X-ray tube 30 and the housing 20 can be shortened, as compared with the case where the insulating member 6a is not provided. Thus, the X-ray tube assembly can be made smaller. In addition, the X-ray tube assembly can be made smaller and have a high durability against voltage; that is, the reduction of the size and the improvement of the durability can be achieved at the same time. Furthermore, as described above, it is possible to conduct the confirmation test with the X-ray tube unit 5 alone to confirm the durability against voltage, and omit the confirmation test to confirm the durability against voltage, with the X-ray tube unit 5 incorporated into the housing 20.

Furthermore, the shield structure 6 forms the flow-path formation body in which the coolant 7 flows.

The shield structure 6 (the insulating member 6a) and the envelope 31 form a coolant flow path in which a natural convection or forced convection of the coolant 7 occurs. In this case, local overheating easily occurs in the X-ray tube 30, as compared with the case where the coolant flow path is not provided; and the thermal dissipation of the anode target 35 can thus be improved.

Also, the shield structure 6 (the insulating member 6a and the X-ray shielding member 6b) forms along with the housing 20 a coolant flow path in which a natural convection or forced convection of the coolant 7 occurs. In this case, it is possible to reduce local overheating in the housing 20, as compared with the case where the coolant flow path is not provided; and the heat transfer from the coolant 7 to the housing 20 can be improved.

(7) Due to provision of the circulation unit 23, the following advantages can be obtained:

The X-ray tube assembly includes the circulation unit 23, which can cause a forced convection of the coolant 7 to occur in the housing 20. It is therefore possible to improve dissipation of heat radiated from the anode target 35. Furthermore, it is possible to reduce overheating of the envelope 31, and also reduce occurrence of discharge at the X-ray tube 30. Also, it is possible to uniformize the temperature of the coolant 7 in the housing 20, and improve the heat transfer from the coolant 7 to the housing 20.

(8) Due to provision of the radiating fins 120, the following advantage can be obtained:

The total surface area of the main body 20e and the radiating fins 120 is greater than the surface area of only the main body 20e. This can increase the area of part of the airway AW which contacts air, and thus improve the cooling performance of the X-ray tube assembly.

(9) Due to provision of the air filter 180, the following advantages can be obtained:

The air filter 180 can remove dust contained in air. Thus, the air induction unit 150 can guide clean air which has passed through the air filter 180 into the airway AW. Due to this, for example, space (ventilation portion) between the radiating fins 120 is not easily blocked, and lowering of the radiation performance of the housing 20 and the radiating fins 120, which serve as a radiator, can be restricted. Thereby, it is possible to reduce the number of times the radiating fins 120, etc. should be maintained (cleaned), improve the workability of the maintenance or achieve maintenance-free.

By virtue of the above, it is possible to achieve a rotating-anode X-ray tube assembly which is smaller in size, improved in safety and made at a lower manufacturing cost, and has a good cooling performance for the X-ray tube 30. Also, it is possible to improve manufacturing yield of rotating-anode X-ray tube assemblies.

Next, a rotating-anode X-ray tube assembly of a second embodiment will be explained. In the second embodiment, elements identical to those in the first embodiment will be denoted by the same reference numerals as in the first embodiment, and its detailed explanations will be omitted. FIG. 5 is a cross-sectional view of the X-ray tube assembly of the second embodiment.

As shown in FIG. 5, an insulating member 6a is formed in the shape of a cylinder having a uniform diameter. In the second embodiment, the insulating member 6a surrounds the entire envelope 31. A given portion of the insulating member 6a is relatively positioned with respect to a housing 20 by a fixing member 90, rubber members 92, etc., and another portion of the insulating member 6a is relatively positioned with respect the housing 20 by a fixing member 140. The fixing member 140 can be formed of an elastic material such as rubber.

It should be noted that metal fittings attached to a stator coil 9 are fixed to the insulating member 6a. Furthermore, the insulating member 6a includes a through hole for a high-voltage cable 61, a through hole serving as a flow path for a coolant 7, etc.

The X-ray tube assembly includes a high-voltage insulating member 4. The high-voltage insulating member 4 is fixed to an X-ray tube 30 by a connection member 40. The high-voltage insulating member 4 and the connection member 40 are mechanically firmly connected to each other. One of ends of the high-voltage insulating member 4 is conically formed, and the other is tubularly formed. The high-voltage insulating member 4 surrounds the small-diameter portion and intermediary portion of a vacuum envelope 31 in the direction perpendicular to the axis a. The high-voltage insulating member 4 electrically insulates between a fixed shaft 1 and the housing 20, and between the fixed shaft 1 and the stator coil 9.

The high-voltage insulating member 4 includes an opening for entrance and exit of the coolant 7, which is located close to the connection member 40. The high-voltage insulating member 4 is also provided to serve as a flow-path formation body between the high-voltage insulating member 4 and the envelope 31, which forms a flow path for the coolant 7. This is because a natural convection occurs at least in the coolant 7 in the housing 20. It should be noted that in the second embodiment, the X-ray tube assembly includes a circulation unit 23, and thus in the coolant 7, a forced convection largely occurs.

Furthermore, in the second embodiment, the insulating member 6a and the high-voltage insulating member 4 are formed independent of each other, and located apart from each other. Thus, the flow path between the insulating member 6a and the envelope 31 is separated from that between the high-voltage insulating member 4 and the envelope 31, as a result of which a natural convection easily occur in the coolant 7.

It should be noted that the stator coil 9 is adhered to the high-voltage insulating member 4.

Figure 6:
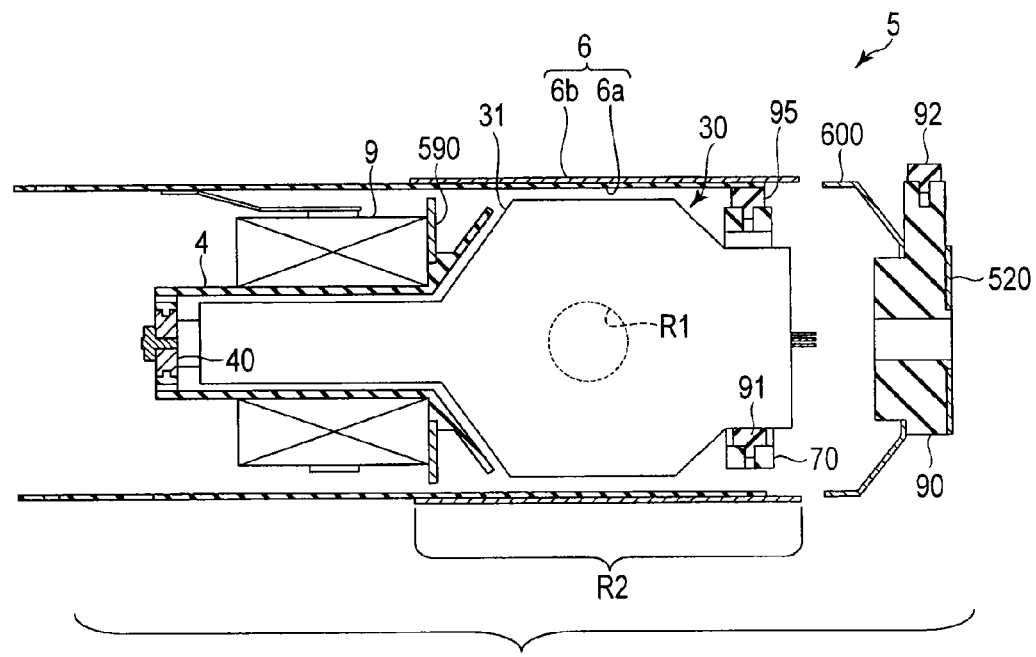
FIG. 6 is a cross-sectional view showing a rotating-anode X-ray tube unit of the second embodiment.

As shown in FIG. 6, at least the X-ray tube 30 and a shield structure 6 form a rotating-anode X-ray tube unit 5. In the second embodiment, the X-ray tube unit 5 is made up of the X-ray tube 30, the shield structure 6, an annular portion 70, a fixing member 90, an X-ray shielding member 600, an X-ray shielding member 520, rubber members 91, 92 and 95, the connection member 40, the high-voltage insulating member 4, the stator coil 9 and an X-ray shielding member 590.

Figure 7:
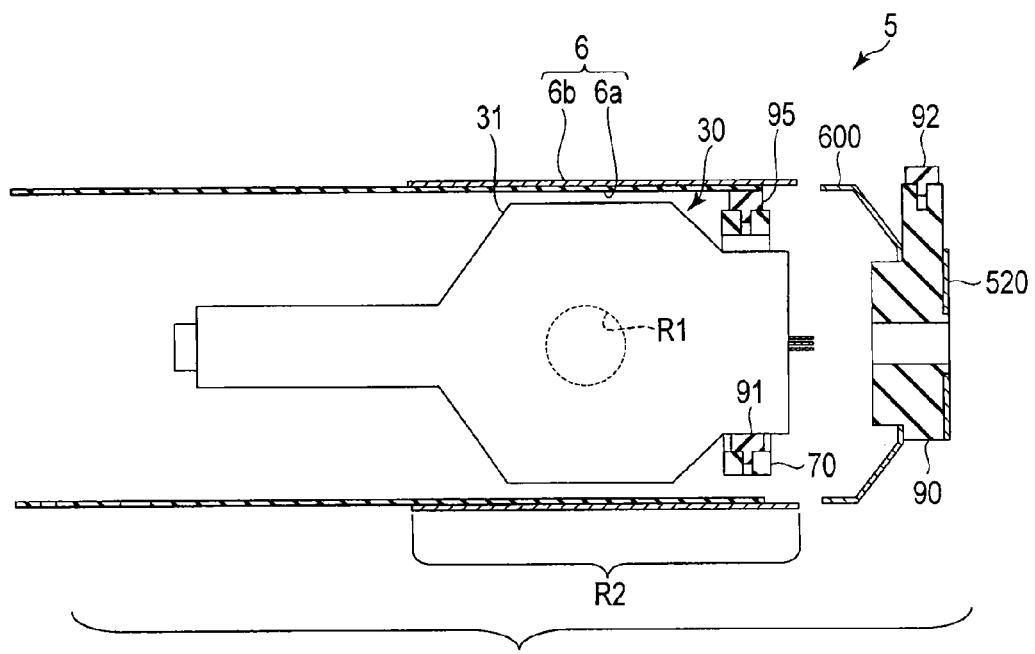
FIG. 7 is a cross-sectional view showing a modification of the rotating-anode X-ray tube unit in the rotating-anode X-ray tube assembly of the second embodiment.

It should be noted that as shown in FIG. 7, the X-ray tube unit 5 may be made up of the X-ray tube 30, the shield structure 6, the annular portion 70, the fixing member 90, the X-ray shielding member 600, the X-ray shielding member 520 and the rubber members 91, 92 and 95.

The rotating-anode X-ray tube assembly of the second embodiment as described above is formed to have substantially the same structure as the X-ray tube assembly of the first embodiment, and can obtain the same advantages as the X-ray tube assembly of the first embodiment.

The X-ray tube unit 5 is formed to cause a natural convection to easily occur in the coolant 7. It is therefore possible to form an X-ray tube assembly in which local overheating does not easily occur in the X-ray tube 30, without a circulation unit 23.

By virtue of the above, it is possible to achieve a rotating-anode X-ray tube assembly which is smaller in size, improved in safety and made at a lower manufacturing cost, and has a good cooling performance for the X-ray tube 30. Also, it is possible to improve manufacturing yield of rotating-anode X-ray tube assemblies.

Figure 8:
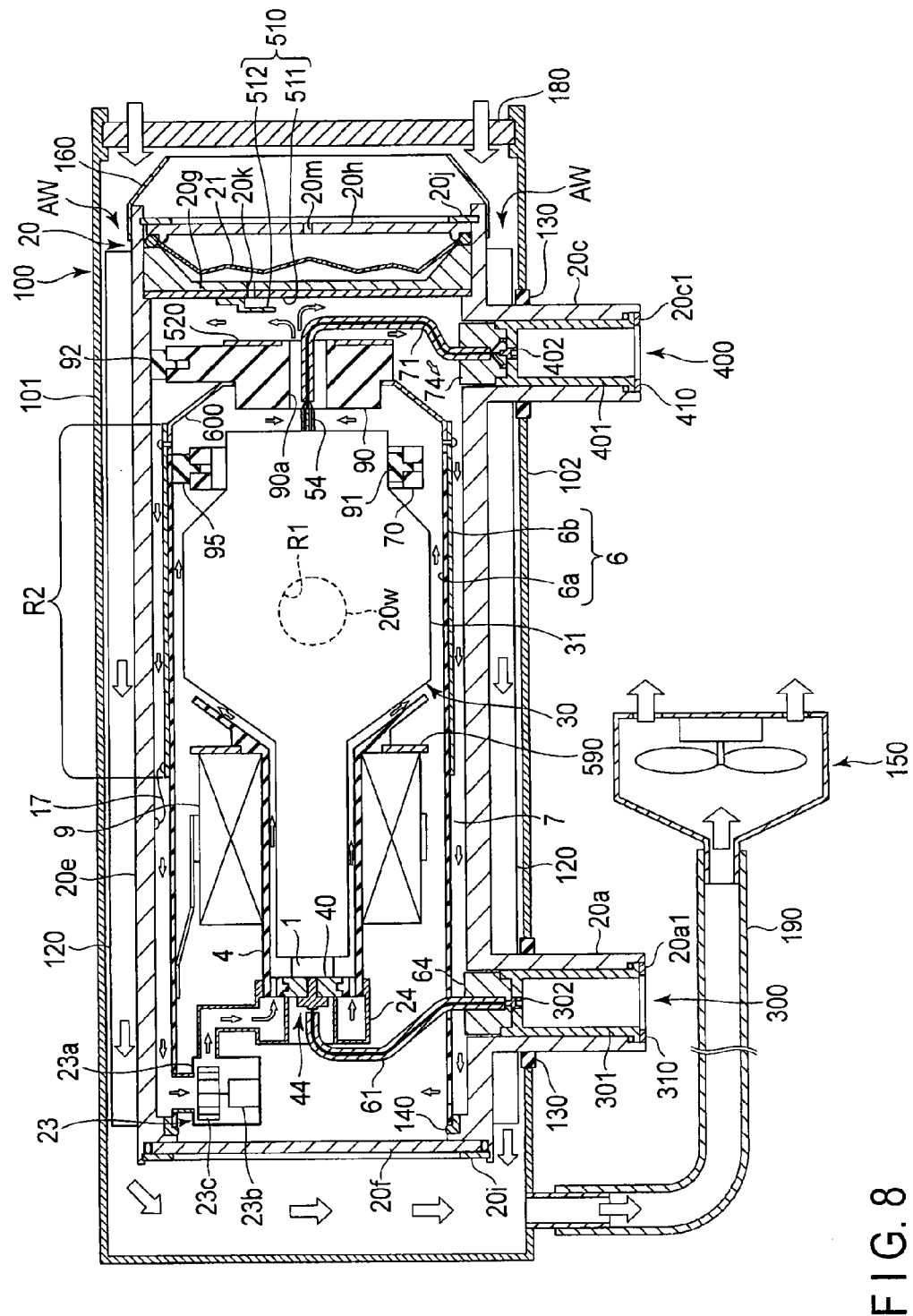
FIG. 8 is a cross-sectional view showing a rotating-anode X-ray tube assembly of a third embodiment.

A rotating-anode X-ray tube assembly of a third embodiment will be explained. With respect to the third embodiment, elements identical to those in the second embodiment will be denoted by the same reference numerals as in the second embodiment, and their detailed explanations will be omitted. FIG. 8 is a cross-sectional view of the X-ray tube assembly of the third embodiment.

As shown in FIG. 8, the X-ray tube assembly is formed without providing a diffusion guide 170. A shell 100 is cylindrically formed to have an end air-tightly closed, and extend in parallel with the axis a. Also, the shell 100 includes ventilation holes at its both end portions. In the third embodiment, of the ventilation holes, the ventilation hole formed on the leeward side of the shell 100 is open in the direction perpendicular to the axis a.

An air induction unit 150 is provided apart from the main body of the X-ray tube assembly, the shell 100, etc.

The X-ray tube assembly further comprises an air duct 190. The air duct 190 is formed of a conduit such as a hose. The air duct 190 air-tightly connects the ventilation hole formed at one end of the shell 100 and the air induction unit 150.

The rotating-anode X-ray tube assembly of the third embodiment as described above has substantially the same structure as the X-ray tube assembly of the second embodiment, and can obtain the same advantages as the X-ray tube assembly of the second embodiment.

It is possible to adjust the distance between the air induction unit 150 and the main body of the X-ray tube assembly by adjusting the length of the air duct 190. This reduces the noise of wind in the vicinity of the main body of the X-ray tube assembly.

Furthermore, the air induction unit 150 can be variously modified. For example, it is possible to apply any of various kinds of air induction units 150 without associating it with the shape of the shell 100.

By virtue of the above, it is possible to achieve a rotating-anode X-ray tube assembly which is smaller in size, improved in safety and made at a lower manufacturing cost, and has a good cooling performance for the X-ray tube 30. Also, it is possible to improve manufacturing yield of rotating-anode X-ray tube assemblies.

Next, a rotating-anode X-ray tube assembly of comparative example 1 will be explained.

Figure 9:
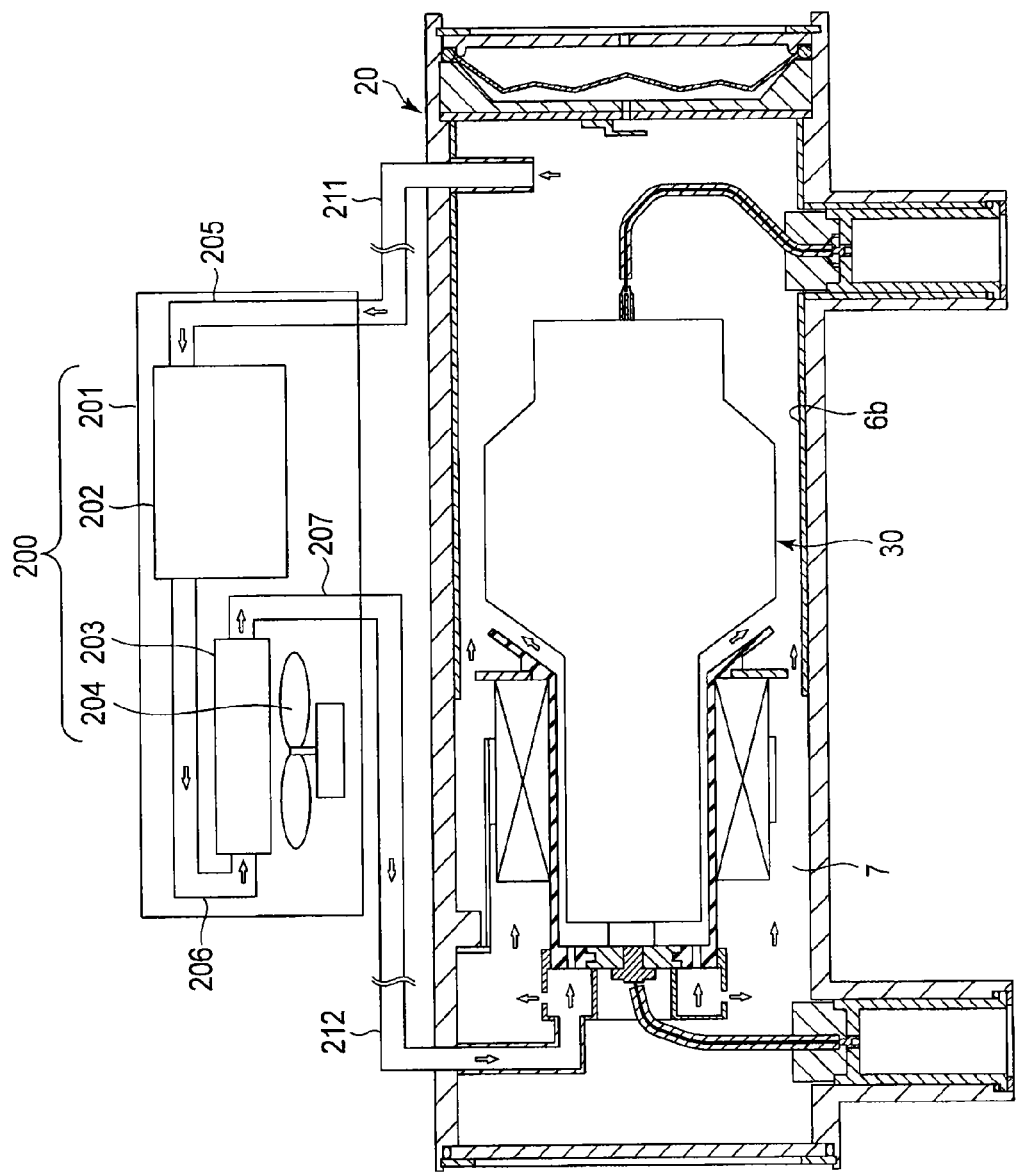
FIG. 9 is a cross-sectional view showing a rotating-anode X-ray tube assembly of comparative example 1.
Figure 10:
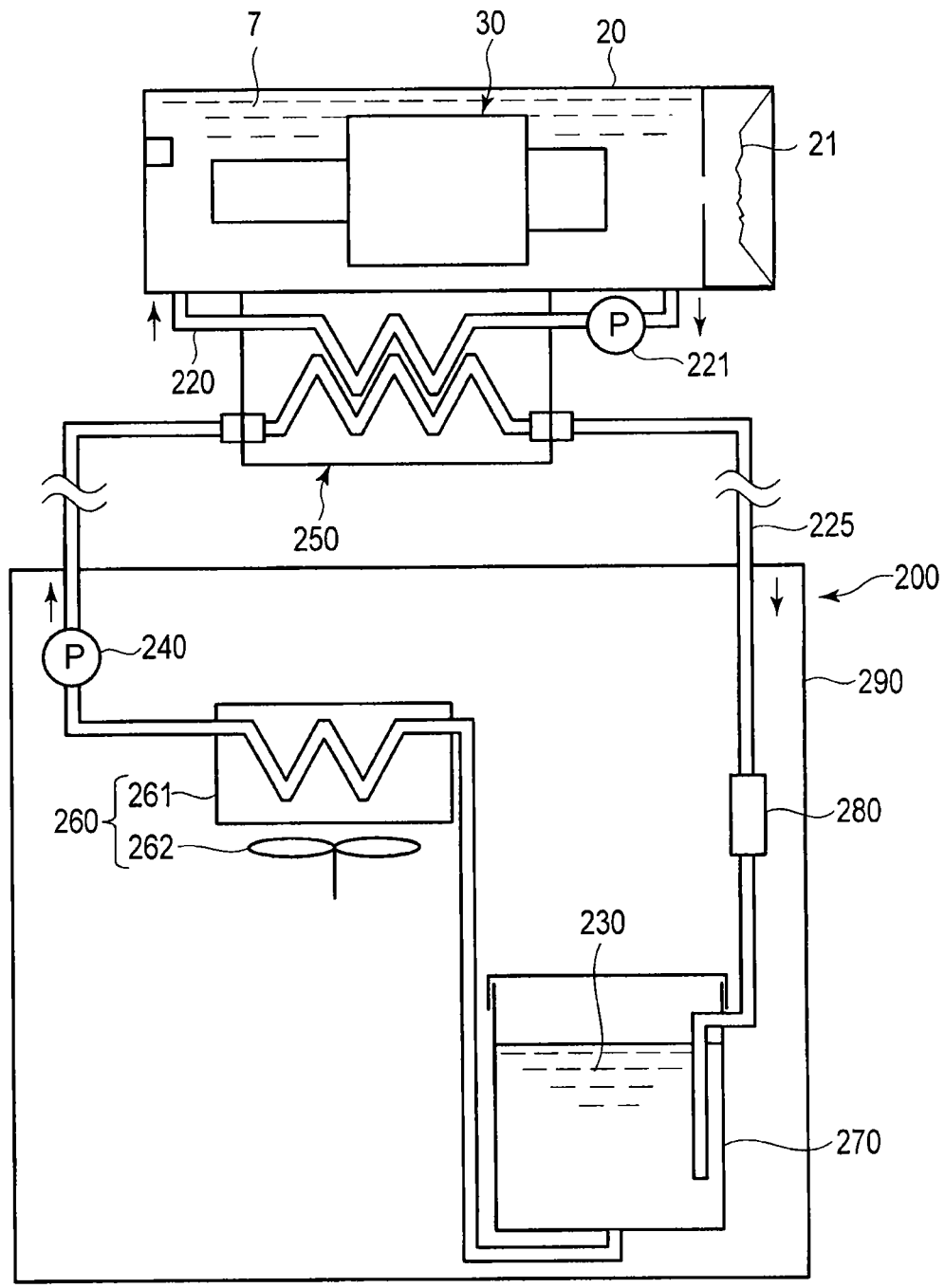
FIG. 10 is a schematic configuration view showing a rotating-anode X-ray tube assembly of comparative example 2.

If the X-ray tube assembly of comparative example 1 is compared with the X-ray tube assemblies according to the above embodiments, roughly speaking, it differs from the X-ray tube assemblies of the above embodiments as follows:

As shown in FIG. 9, the X-ray tube assembly of comparative example 1 is formed without providing the insulating member 6a, the circulation unit 23, the shell 100, the air induction unit 150 and the air filter 180.

An X-ray shielding member 6b is formed by bonding a lead plate to an inner surface of a housing 20. Thus, the X-ray tube assembly of comparative example 1 has the following problems: usage of lead (X-ray shielding material) cannot be reduced; the manufacturing cost cannot be lowered; and an X-ray shielding member 6b of comparative example 1 cannot prevent leakage of X rays.

In comparative example 1, the X-ray tube assembly comprises an air-cooling type of cooler unit 200. The cooler unit 200 comprises a housing 201, a circulation pump 202 and a heat exchanger (air-cooled radiator 200 and a fan 204). The housing 20 and the circulation pump 202 are connected to each other by a conduit 211 and a conduit 205 provided in the housing 201. The circulation pump 202 and an air-cooled radiator 203 are connected to each other by a conduit 206 provided in the housing 201. The air-cooled radiator 203 and the housing 20 are connected to each other by conduit 207 provided in the housing 201 and conduit 212.

In comparative example 1, in order to enhance the function of the heat exchanger, it is necessary to increase the surface area of the air-cooled radiator 203. Thus, since the cooler unit needs to have a certain volume or more, it is not possible to achieve a compact X-ray apparatus.

For the above reason, in comparative example 1, it is impossible to achieve an X-ray tube assembly which is smaller in size and made at a lower cost. Also, it is impossible for comparative example 1 to improve manufacturing yield of rotating-anode X-ray tube assemblies.

Next, a rotating-anode X-ray tube assembly of comparative example 2 will be explained.

As shown in 10, the X-ray tube assembly of comparative example 2 comprises an X-ray tube 30, a housing 20, a coolant 7, a circulation flow path 220, a circulation pump 221, a circulation flow path 225, an water-based coolant 230, a circulation pump 240, heat exchangers 250 and 260, a tank 270, a flow sensor 280 and a housing 290. The heat exchanger 260 includes a radiator 261 and a fan unit 262.

The X-ray tube assembly includes a water-cooling type of cooler unit 200. The heat exchanger 250 includes circulation flow paths 220 and 225. The heat exchanger 250 is, for example, a plate type heat exchanger. The heat exchanger 250 transmits heat of the coolant 7 to the coolant 230. Therefore, the coolant 7 is a primary coolant which cools the X-ray tube 30, and the coolant 230 is a secondary coolant which cools the coolant 7 (primary coolant).

However, in the X-ray tube assembly of comparative example 2, it is necessary to provide two heat exchangers, i.e., the heat exchangers 250 and 260. In order to enhance the function of the heat exchanger 260, it is necessary to increase the surface area of the radiator 261. Furthermore, the cooler unit 200 includes the tank 270, which stores the coolant 230. Since the cooler unit 200 needs to have a given volume or more, it is not possible to achieve a compact X-ray apparatus.

For the above reason, in comparative example 2, although the X-ray tube assembly has a good cooling performance for the X-ray tube 30, it cannot be made smaller.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, in each of the above embodiments, the X-ray tube assembly comprises the circulation unit 23. However, the structure of each embodiment is not limited to such a structure; that is, it can be variously modified. It may be formed without the circulation unit 23. The X-ray tube unit 5 is formed to cause a natural convection to easily occur in the coolant 7. Thus, the X-ray tube assembly can also be made such that local overheating not easily occur in the X-ray tube 30 without the circulation unit 23. It is preferable that a sufficient gap (approximately 0.2 mm or more) be provided between the shield structure 6 and an inner wall of the main body 20e to cause a flow of the coolant 7 to be produced due to the natural convection. In order to do so, according to circumstances, the shape (outside diameter) of the shield structure 6 may be changed.

The shapes of the radiating fins 120 can be variously changed. For example, the radiating fins 120 may be spirally shaped and thus spirally extend around the housing 20. On the other hand, if the radiating fins 120 are annularly shaped and formed coaxial with the housing 20, they reduce the velocity of an air flow in the airway AW. Such a shape is thus undesired.

Furthermore, the X-ray tube assembly may be formed without providing the radiating fins 120.

The position of the air induction unit 150 is not limited to the position described by way of with respect to each of the embodiments; that is, the air induction unit 150 can be located in various positions. For example, the air induction unit 150 may be located between the air filter 180 and the airway AW (it may be located inward of the air filter 180) or may be located outward of the air filter 180.

In each of the above embodiments, the X-ray tube assembly includes the air filter 180. However, its structure is not limited to such a structure; that is, it can be variously modified. For example, the X-ray tube assembly may be formed without including the air filter 180.

In each of the above embodiments, the X-ray tube assembly includes the contraction guide 160 and the diffusion guide 170. However, its structure is not limited to such a structure; that is, it can be variously modified. For example, the X-ray tube assembly may be formed without including the contraction guide 160 or the diffusion guide 170.

In the case where the housing 20 is formed of metal, it may be formed of material other than aluminum. As the material, for example, an aluminum alloy, a magnesium alloy, stainless or brass can be selected.

In order to increase the mechanical strength of the electrical insulating material of the housing 20 or the insulating member 6a, the electrical insulating material may be made to contain reinforcing fibers such as glass fibers, carbon fibers, boron fibers, alumina fibers or aramid fibers.

The X-ray tube assembly is not limited to a neutral-point grounded type of X-ray tube assembly in which a neutral point between an anode target 35 and a cathode 36 is grounded. For example, as the X-ray tube assembly, an anode grounded type of X-ray tube assembly or a cathode grounded type of X-ray tube assembly may be applied. In the anode grounded type of X-ray assembly, an anode target 35 is grounded. In the cathode grounded type of X-ray tube assembly, a cathode 36 is grounded.

The embodiments described above can be applied to various kinds of rotating-anode X-ray tube assemblies.

What is claimed is:

1. A rotating-anode X-ray tube assembly comprising:
   a rotating-anode X-ray tube comprising a cathode configured to emit electrons, an anode target configured to emit X rays, a supporting mechanism which supports the anode target in such a way as to allow the anode target to be rotated, and an envelope which accommodates the cathode, the anode target and the supporting mechanism;
   a housing which accommodates the rotating-anode X-ray tube;
   a coolant filled in space between the rotating-anode X-ray tube and the housing;
   a first shell provided between the envelope and the housing and apart from the envelope and the housing, extending along an axis of the anode target, and surrounding the envelope;
   an X-ray shielding member fixed to the first shell, provided between the first shell and the housing and apart from the housing, and including a through hole through which the X rays are made to pass;
   a second shell provided apart from the housing, surrounding the housing in a direction perpendicular to the axis, and forming an airway between the second shell and the housing; and
   an air induction unit configured to introduce air into the airway to produce a flow of air.

2. The rotating-anode X-ray tube assembly of claim 1, further comprising:
   a circulation unit,
   wherein
   the X-ray shielding member is shaped to be in to contact with or in vicinity to the first shell, and forms a flow-path formation body which flows the coolant, and
   the circulation unit causes the coolant to flow in a given direction parallel to the axis, in a coolant flow path between the flow-path formation body and the housing, or the flow-path formation body and the envelope.

3. The rotating-anode X-ray tube assembly of claim 1, wherein
   the housing is formed of an electrical conductor, and
   the X-ray shielding member is electrically connected to the housing.

4. The rotating-anode X-ray tube assembly of claim 1, further comprising:
   a plurality of radiating fins provided in the airway and at an outer surface of the housing.

5. The rotating-anode X-ray tube assembly of claim 4, wherein
the radiating fins are formed of plate-like members extending in a direction parallel to the axis.

6. The rotating-anode X-ray tube assembly of claim 1, wherein
the second shell is made up of a plurality of divided portions.

7. The rotating-anode X-ray tube assembly of claim 6, wherein
the divided portions are separated from each other in a direction perpendicular to the axis.

8. The rotating-anode X-ray tube assembly of claim 7, wherein
the second shell is fixed to the housing by an elastic body interposed between the second shell and the housing.

9. The rotating-anode X-ray tube assembly of claim 6, wherein
the second shell is fixed to the housing by an elastic body interposed between the second shell and the housing.

10. The rotating-anode X-ray tube assembly of claim 1, wherein
the second shell is fixed to the housing by an elastic body interposed between the second shell and the housing.

11. The rotating-anode X-ray tube assembly of claim 1, wherein
the first shell entirely surrounds the anode target along an axis of the anode target.

12. The rotating-anode X-ray tube assembly of claim 1, wherein the first shell is an electrical insulating member.

13. The rotating-anode X-ray tube assembly of claim 1, further comprising:
a spacer provided between the housing and the second shell,
wherein the spacer holds the airway open.

14. The rotating-anode X-ray tube assembly of claim 1, wherein
the second shell is formed in a shape of a cylinder including vents at both end portions of the second shell, and extends in a direction parallel to the axis, and
the air induction unit is attached to one of the both end portions of the second shell.

15. The rotating-anode X-ray tube assembly of claim 14, further comprising:
an air filter which is located windward with respect to the airway and attached to the second shell, permits air to pass through the air filter, and is configured to remove dust contained in the air,
wherein
the air induction unit is configured to introduce the air transmitted through the air filter into the airway.

16. The rotating-anode X-ray tube assembly of claim 1, further comprising:
an air duct,
wherein
the second shell is formed in a shape of a cylinder including vents at both end portions of the second shell, and extends in a direction parallel to the axis, and
the air duct connects the air induction unit and the vent of one of the both end portions of the second shell.

17. The rotating-anode X-ray tube assembly of claim 16, further comprising:
an air filter which is located upstream with respect to the airway and attached to the second shell, permits air to pass through the air filter, and is configured to remove dust contained in the air,
wherein
the air induction unit is configured to introduce the air transmitted through the air filter into the airway.

* * * * *